US00PP10419P

United States Patent [19]

Pieters

[11] Patent Number: Plant 10,419

[45] Date of Patent: May 26, 1998

[54] CHRYSANTHEMUM PLANT NAMED 'OZENDA'

[76] Inventor: Dirk Pieters, Schierveldestraat 3A Oosnieuwkerke, 8840 Staden, Belgium

[21] Appl. No.: 752,151

[22] Filed: Nov. 19, 1996

[51] Int. Cl.[6] ..... A01H 5/00

[52] U.S. Cl. ..... Plt./76

[58] Field of Search ..... Plt./74.1, 76, 80, Plt./82.4

[56] References Cited

U.S. PATENT DOCUMENTS

P.P. 6,838 6/1989 Hesse ..... Plt./76

*Primary Examiner*—Howard J. Locker
*Attorney, Agent, or Firm*—C. A. Whealy

[57] ABSTRACT

A distinct cultivar of Chrysanthemum plant named 'Ozenda', characterized by its spherical and mounded plant habit; moderate vigor and growth rate; decorative-type inflorescences with slight open center; light lavender ray florets; numerous inflorescences per plant; and good garden performance.

3 Drawing Sheets

The present invention relates to a new and distinct cultivar of garden Chrysanthemum plant, botanically known as *Dendranthema grandiflora* and referred to by the cultivar name Ozenda.

The new cultivar is a product of a planned breeding program conducted by the inventor in Staden, Belgium. The objective of the breeding program was to create new garden Chrysanthemum cultivars that are freely branching and have numerous and long-lasting inflorescences.

The new cultivar originated from a cross made by the inventor in 1993 of the nonpatented cultivar Veria Rose as the female, or seed, parent with the nonpatented cultivar Quick Marie as the male, or pollen, parent.

The new Chrysanthemum was discovered and selected by the inventor as a flowering plant within the progeny of the stated cross in a controlled environment in Staden, Belgium.

Asexual reproduction of the new cultivar by terminal cuttings taken at Staden, Belgium, has shown that the unique features of this new Chrysanthemum are stable and reproduced true to type in successive generations.

The following traits have been repeatedly observed and are determined to be the unique characteristics of 'Ozenda'. These characteristics in combination distinguish 'Ozenda' as a new and distinct cultivar:

1. Spherical and mounded plant habit, moderate vigor and growth rate, and freely branching.
2. Decorative-type inflorescences with slight open center.
3. Light lavender ray florets.
4. Numerous inflorescences per plant.
5. Good garden performance.

The cultivar Ozenda has not been observed under all possible environmental conditions. The phenotype may vary somewhat with variations in environment such as temperature, daylength and light intensity, without, however, any variance in genotype.

In side-by-side comparisons in Staden, Belgium, under commercial practice, plants of the new Chrysanthemum differ from plants of the female parent, the cultivar Veria Rose, in plant size, foliage color and inflorescence size. In the same comparisons, plants of the new Chrysanthemum differ from the male parent, the cultivar Quick Marie, in ray floret color, inflorescence type and plant size.

Plants of the new Chrysanthemum can be compared to the cultivar Lynn (U.S. Plant Pat. No. 8,171). However, in side-by-side comparisons conducted in Oxnard, Calif., under commercial practice, plants of the new Chrysanthemum differed from plants of the cultivar Lynn in the following characteristics:

1. Plants of the new Chrysanthemum are spherical whereas plants of the cultivar Lynn are more upright and mounding.
2. Plants of the new Chrysanthemum are more freely branching than plants of the cultivar Lynn.
3. Plants of the new Chrysanthemum have larger leaves but fewer leaves per lateral stem than plants of the cultivar Lynn.
4. Inflorescences of plants of the new Chrysanthemum are smaller but more numerous than inflorescences of plants of the cultivar Lynn.
5. When opening, ray florets of plants of the new Chrysanthemum have yellow apices and are paler in color than ray florets of plants of the cultivar Lynn.
6. Plants of the new Chrysanthemum have weaker and longer peduncles than plants of the cultivar Lynn.

A detailed comparison of plants of the new Chrysanthemum and the cultivar Lynn appears in Chart A at the end of the specification.

The accompanying colored photographs illustrate the overall appearance of the new cultivar, showing the colors as true as it is reasonably possible to obtain in colored reproductions of this type.

The first photograph comprises a side perspective view of a typical flowering 16.5-cm container of 'Ozenda' with five cuttings in the container.

The second photograph comprises a close-up view of typical inflorescences of the new Chrysanthemum.

The third photograph comprises a close-up view of five leaves at different stages of development and a fully opened inflorescence. Foliage and floret colors in the photographs may appear different from the actual colors due to light reflectance.

In the following description, color references are made to The Royal Horticultural Society Colour Chart except where general terms of ordinary dictionary significance are used. The following observations and measurements describe plants grown in Oxnard, Calif., under commercial practice in a glass-covered greenhouse with night temperatures ranging between 14 and 20C, day temperatures ranging between 20 and 30C, and average light levels of 5,000 to 6,000 footcandles.

After sticking unrooted cuttings of the new cultivar, plants receives 4 weeks of long day/short nights followed by short day/long nights until flowering. Measurements and numerical values represent ranges or averages for six typical flowering plants.

Botanical classification: *Dendranthema grandiflora* cultivar Ozenda.

Commercial classification: Garden chrysanthemum.

Parentage:

*Female, or seed, parent.*—*Dendranthema grandiflora* cultivar Veria Rose (not patented).

*Male, or pollen, parent.*—*Dendranthema grandiflora* cultivar Quick Marie (not patented).

Propagation:

*Type.*—Terminal tip cuttings.

*Time to rooting.*—10 to 12 days with soil temperatures of 20C.

*Rooting habit.*—Fine, fibrous and well-branched.

Plant description:

*Appearance.*—Perennial herbaceous garden plant. Spherical and rounded growth habit. Moderate growth rate and vigor and freely branching.

*Plant height.*—About 18 cm.

*Lateral branch length.*—About 16 cm.

*Quantity of lateral branches after removal of apical meristem.*—About 6.

*Stem color.*—146C.

*Foliage description.*—Number of leaves per plant: About 53. Number of leaves per lateral branch: About 11. Leaf arrangement: Alternate. Leaf size, fully expanded: Length: About 5 cm. Width: About 4.2 cm. Leaf apex: Apiculate. Leaf base: Attenuate. Leaf margin: Palmately lobed. Leaf texture: Abaxial and adaxial surfaces slightly pubescent, smooth and dull. Veins prominent on abaxial surface. Petiole length: About 2.3 cm. Color: Young foliage adaxial surface: 147A. Young foliage abaxial surface: 147B. Fully expanded foliage adaxial surface: 147A. Fully expanded foliage abaxial surface: 147B. Venation adaxial surface: 147C. Venation abaxial surface: 147B. Petiole: 147C.

Inflorescence description:

*Appearance.*—Decorative button-type inflorescence form with slight open center. Inflorescences borne on terminals about foliage, arising from leaf axils. Disc and ray florets arranged acropetally on a flat capitulum.

*Flowering response.*—Under natural conditions, plants flower in the autumn. Inflorescence initiation and development can be induced under short day/long night conditions (at least 13.5 hours of darkness). Plants exposed to 3 or 4 weeks of long day/short night conditions after sticking followed by photoinductive short day/long night conditions, flower about 49 days later. Inflorescences maintain good substance for three weeks under bright natural daylight.

*Quantity of inflorescences.*—About 7 inflorescences per flowering stem.

*Inflorescence size.*—Diameter: About 3.4 cm. Depth (height): About 1.1 cm. Diameter of disc: About 3 mm.

*Opening inflorescences.*—Bud shape: Spherical. Bud size: Length: About 6 mm. Width: About 6 mm. Bud color: 75C.

*Ray florets.*—Shape: Oval. Size: Length: About 1.35 cm. Width: About 7 mm. Apex: Slightly dentate. Base: Acute. Margin: Entire. Texture: Matte, smooth and glabrous. Aspect: Flat. Number of ray florets per inflorescence: About 120. Color: When opening, adaxial surface: 75D with yellow, 13C, apex. When opening, abaxial surface: 75C. Mature, adaxial surface: 76D. Mature, abaxial surface: 69D. Fading to: 69D.

*Disc florets.*—Shape: Tubular. Size: Length: About 4 mm. Width: About 1 mm. Number of disc florets per inflorescence: About 12. Color: Immature: 154D. Mature: 154C.

*Peduncle.*—Aspect: Weak, angled about 35° to 40° to the stem. Length: First peduncle: About 3.7 cm. Fourth peduncle: About 5.6 cm. Texture: Pubescent. Color: 137C.

*Reproductive organs.*—Androecium: Present on disc florets only. Anther color: 7A. Pollen: Moderate, 7A in color. Gynoecium: Present on both ray and disc florets. Style color: 2B.

Disease resistance: No known Chrysanthemum diseases observed to date on plants grown under commercial greenhouse conditions.

Seed production: Seed production has not been observed.

CHART A

| CHARACTERISTIC | 'OZENDA' | 'LYNN' |
|---|---|---|
| PLANT SHAPE | Spherical, rounded | Mounding |
| PLANT HEIGHT | About 18 cm | About 21 cm |
| LATERAL STEM LENGTH | About 16 cm | About 17 cm |
| QUANTITY OF LATERAL BRANCHES AFTER PINCHING | About 6 | About 3 to 4 |
| QUANTITY OF LEAVES PER LATERAL BRANCH | About 11 | About 16 |
| LEAF LENGTH | About 5 cm | About 3.6 cm |
| LEAF WIDTH | About 4.2 cm | About 3.6 cm |
| LEAF APEX | Apiculate | Round, very slightly apiculate |
| PETIOLE LENGTH | About 2.3 cm | About 1.7 cm |
| YOUNG FOLIAGE COLOR, ADAXIAL SURFACE | 147A | 137A |
| YOUNG FOLIAGE COLOR, ABAXIAL SURFACE | 147B | 137B |
| MATURE FOLIAGE COLOR, ADAXIAL SURFACE | 147A | 137A |
| MATURE FOLIAGE COLOR, ABAXIAL SURFACE | 147B | 137B |
| QUANTITY OF INFLORESCENCES PER LATERIAL STEM | About 7 | About 4 to 5 |
| INFLORESCENCE FORM | Decorative button with open center | Decorative with slight open center as inflorescence develops |
| INFLORESCENCE DIAMETER | About 3.4 cm | About 4.2 cm |
| INFLORESCENCE HEIGHT | About 1.1 cm | About 1.3 cm |
| BUD COLOR | 75C | 75A |
| RAY FLORET SHAPE | Oval | Obovate |
| RAY FLORET ASPECT | Flat | Edges curl upward |
| RAY FLORET LENGTH | About 1.35 cm | About 1.8 cm |
| RAY FLORET WIDTH | About 7 mm | About 6.5 mm |
| RAY FLORET COLOR WHEN OPENING, ADAXIAL | 75D with yellow, 13C, apex | 75B |
| RAY FLORET COLOR, WHEN OPENING, ABAXIAL | 75C | 75C |
| RAY FLORET COLOR, MATURE, ADAXIAL | 76D | 75C |

CHART A-continued

| CHARACTERISTIC | 'OZENDA' | 'LYNN' |
|---|---|---|
| RAY FLORET COLOR, MATURE, ABAXIAL | 69D | 75D |
| RAY FLORET COLOR FADING TO | 69D | 75D |
| NUMBER OF RAY FLORETS PER INFLORESCENCE | About 120 | About 190 |
| DISC FLORET COLOR, IMMATURE | 154D | 154C |
| DISC FLORET COLOR, MATURE | 154C | 154C |
| PEDUNCLE STRENGTH | Weak | Strong |
| PEDUNCLE ANGLE | About 35 to 40° | About 45° |

CHART A-continued

| CHARACTERISTIC | 'OZENDA' | 'LYNN' |
|---|---|---|
| PEDUNCLE LENGTH, FIRST | About 3.7 cm | About 2.3 cm |
| PEDUNCLE LENGTH, FOURTH | About 5.6 cm | About 4.5 cm |
| PEDUNCLE COLOR | 137C | 137D |
| ANTHER COLOR | 7A | 14A |
| POLLEN COLOR | 7A | 14A |

It is claimed:

1. A new and distinct cultivar of Chrysanthemum plant named 'Ozenda', as illustrated and described.

* * * * *

PLT-287
C5203 OR PP 010,419 SR
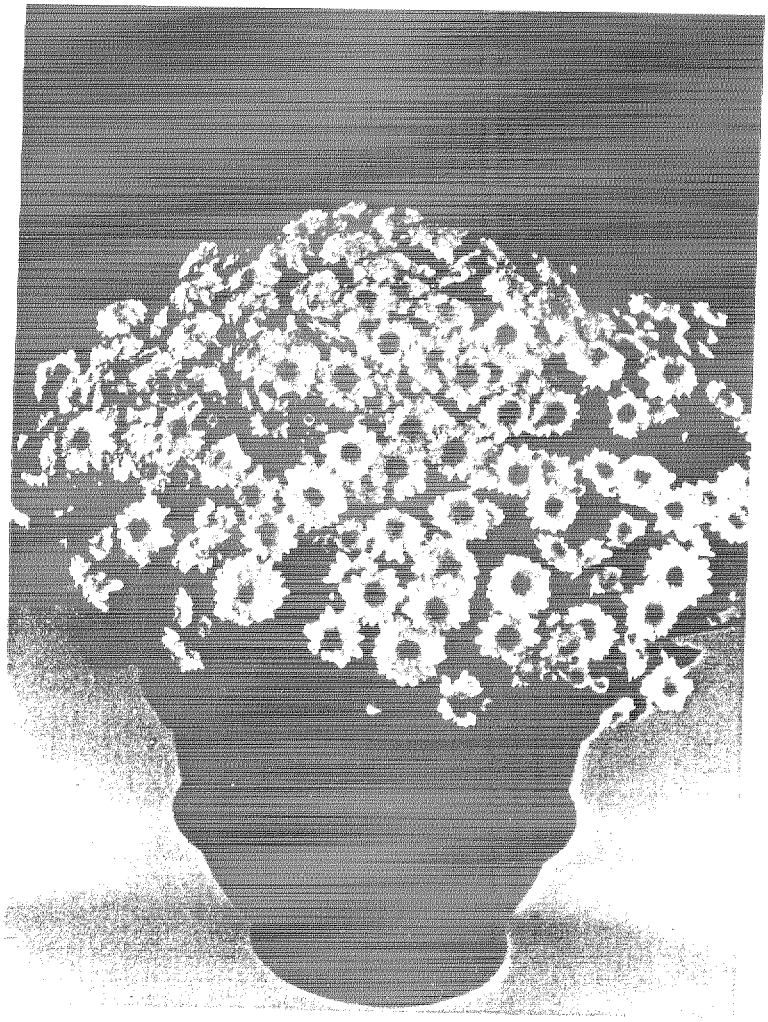

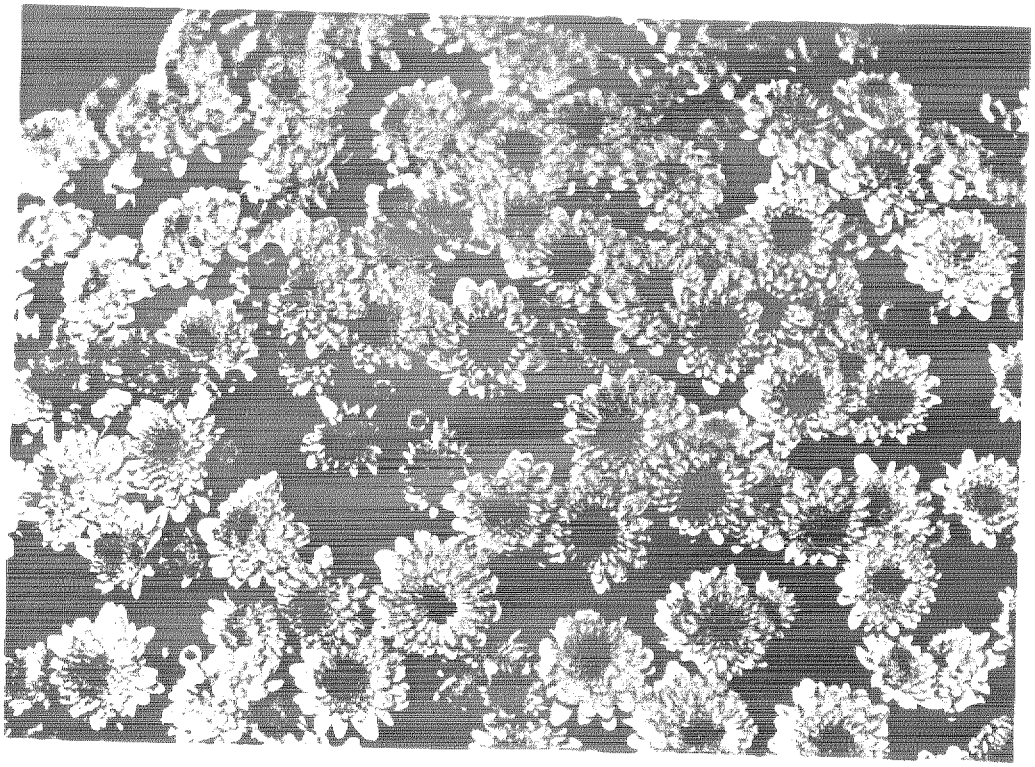

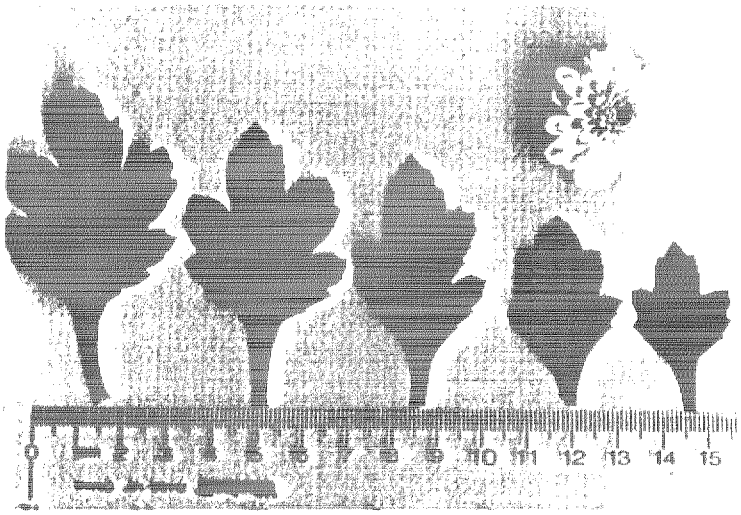
0
10
11
12
13
14
15